(12) United States Patent
Izume et al.

(10) Patent No.: US 9,125,837 B2
(45) Date of Patent: Sep. 8, 2015

(54) PROCESS FOR PRODUCING SILYLATED PULLULAN AND COSMETIC PREPARATION

(75) Inventors: Masato Izume, Ibaraki (JP); Takahiro Fukuhara, Ibaraki (JP); Makoto Niwa, Ibaraki (JP); Takanori Sannan, Tokyo (JP); Shinya Tsuchida, Tokyo (JP); Nobuyuki Kobayashi, Tokyo (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

(21) Appl. No.: 12/531,336

(22) PCT Filed: Mar. 30, 2007

(86) PCT No.: PCT/JP2007/057093
§ 371 (c)(1),
(2), (4) Date: Sep. 15, 2009

(87) PCT Pub. No.: WO2008/126251
PCT Pub. Date: Oct. 23, 2008

(65) Prior Publication Data
US 2010/0048886 A1 Feb. 25, 2010

(51) Int. Cl.
C08B 37/00 (2006.01)
A61K 8/73 (2006.01)
A61Q 1/02 (2006.01)
A61Q 1/08 (2006.01)
A61Q 1/10 (2006.01)
A61Q 3/00 (2006.01)
A61Q 17/04 (2006.01)

(52) U.S. Cl.
CPC ... *A61K 8/73* (2013.01); *A61Q 1/02* (2013.01); *A61Q 1/08* (2013.01); *A61Q 1/10* (2013.01); *A61Q 3/00* (2013.01); *A61Q 17/04* (2013.01); *C08B 37/0018* (2013.01)

(58) Field of Classification Search
None
See application file for complete search history.

(56) References Cited

U.S. PATENT DOCUMENTS 4,004,977 A    1/1977    Kato et al.
7,847,093 B2 * 12/2010   Ludescher et al. ............ 540/222

FOREIGN PATENT DOCUMENTS

| JP | 62-240335 A | 10/1987 |
|---|---|---|
| JP | 07-89834 A | 4/1995 |
| JP | 9-188604 A | 7/1997 |
| JP | 09-188604 A | 7/1997 |
| JP | 2004-244333 A | 9/2004 |

OTHER PUBLICATIONS

Nakae et al. JP 2004/244333A, Sep. 2004, machine translation.*
JP 07-053650 B, 1995, machine translation.*
Chiba et al. JP 62240335A, Oct. 1987, English translation.*
International Search Report for PCT/JP2007/057093 dated Apr. 11, 2007.
The extended European Search Report for the related European patent application No. 07740529.8 dated Nov. 27, 2012.
The Summons to attend oral proceedings for the related European Patent Application No. 07740529.8 dated Jul. 8, 2014.

* cited by examiner

*Primary Examiner* — Layla Bland
(74) *Attorney, Agent, or Firm* — Kenealy Vaidya LLP

(57) ABSTRACT

The present invention provides a process for producing silylated pullulan, which features reacting pullulan with N,O-bistrimethylsilylacetamide by using, as a reaction medium, only one of N-methyl-2-pyrrolidone and N-ethyl-2-pyrrolidone or a mixed solvent of both of them. Compared with conventional processes, the process according to the present invention can produce high-purity silylated pullulan simply, easily and efficiency.

3 Claims, No Drawings

PROCESS FOR PRODUCING SILYLATED PULLULAN AND COSMETIC PREPARATION

This application is a U.S. national phase filing under 35 U.S.C. §371 of PCT Application No. PCT/JP2007/057093, filed Mar. 30, 2007, the entire disclosure of which being incorporated herein.

TECHNICAL FIELD

This invention relates to a production process for silylated pullulan, and more specifically to a production process for silylated pullulan, which is simpler, easier and more efficient than a conventional process.

BACKGROUND ART

Pullulan, a starting raw material for silylated pullulan, is a natural polysaccharide formed of maltotriose units regularly joined together via α-1,6-linkages. This pullulan is excellent in moisturizing properties, adhesion properties and safety, and as a nonionic polymer, is used as various additives.

For example, a derivative obtained by introducing silyl groups as side chains in the nonionic polymer is soluble in silicone oil, and the resulting solution is low in biological irritancy. Therefore, the derivative is expected to find utility in applications such as cosmetics, foods and medicines, and its use as an ingredient in foundations and makeup cosmetic preparations for nails is described in Patent Document 1.

In Patent Document 1, silylated pullulan is also exemplified as a derivative with silyl groups introduced as side chains in the nonionic polymer. Specifically, a process is disclosed, which includes dispersing pullulan in a mixed solvent of pyridine and toluene and then reacting it with triethylbromosilane. In addition, Patent Document 2 describes sunscreen cosmetic preparations with silylated pullulan mixed therein, and Patent Document 3 describes oil-based foundations with silylated pullulan mixed therein.

Patent Document 1: JP-A-62-240335
Patent Document 2: JP-B-3491933
Patent Document 3: JP-A-09-188604

DISCLOSURE OF THE INVENTION

Problems to be Solved by the Invention

Especially in Patent Document 1, a silylation reaction of pullulan in a two-component system making use of pyridine and toluene is exemplified. However, no detailed description is made about a method for the elimination of the used solvents or about a drying step. The process of Patent Document 1, therefore, involves a problem of pollution with an offensive odor especially by the use of pyridine and also a problem of running cost required for a solvent elimination step or about its efficiency.

Patent Documents 2 and 3 disclose the evolution of specific limited applications each of which uses silylated pullulan as a raw material. Neither Patent Document 2 nor Patent Document 3 discloses any detailed application example of silylated pullulan or any process for its production.

Namely, silylated pullulan excellent in water resistance and film-forming property is effectively used as additives to cosmetic products, and further, plays a role as safe additives. Nonetheless, the conventional production process still requires precise contrivance and establishment as to the purification method and production process such as, for example, how to prevent a solvent such as pyridine from remaining, and this precise contrivance and establishment still remains as an important problem.

An object of the present invention is, therefore, to provide a simpler, easier and more efficient process for the production of high-purity silylated pullulan than the conventional process.

Means for Solving the Problem

The above-described object can be achieved by the present invention to be described hereinafter. Described specifically, the present invention provides a process for producing silylated pullulan, which comprises reacting pullulan with N,O-bistrimethylsilylacetamide by using, as a reaction medium, only one of N-methyl-2-pyrrolidone and N-ethyl-2-pyrrolidone or a mixed solvent thereof. In this process, toluene can be used as a diluent upon production.

The present invention also provides a method for purifying silylated pullulan, which comprises dissolving silylated pullulan, which is obtainable by the above-described process of the present invention, in toluene and/or isopropyl alcohol, pouring the resulting solution into methanol to precipitate the silylated pullulan, and desolvating the precipitated silylated pullulan.

The present invention also provides a method for drying silylated pullulan, which comprises repeating once or more an operation that dries, disintegrates and re-dries silylated pullulan obtainable by the above-described process or method of the present invention.

The present invention also provides an oil-based cosmetic preparation comprising silylated pullulan obtainable by the above-described process or method of the present invention.

Advantageous Effects of the Invention

According to the present invention, it is possible to provide a simpler, easier and more efficient process for the production of high-purity silylated pullulan than the conventional process.

BEST MODES FOR CARRYING OUT THE INVENTION

The present invention will next be described in further detail based on best modes for carrying out the invention. Pullulan, which is used as a raw material in the present invention, is available from the market, and its commercial products are all usable. Examples include "PI-10" and "PI-20", trade names, products of Hayashibara Shoji, Inc. On the other hand, N,O-bistrimethylsilylacetamide which is used as a silylating agent in the present invention is also available from the market, and its commercial products are all usable. Examples include "DYNASYLANBSA", trade name, product of Degussa AG. Further, N-methyl-2-pyrrolidone (NMP) and N-ethyl-2-pyrrolidone (NEP), reaction solvents, are well-known industrial products, and are available from the market. Their commercial products are all usable.

The process of the present invention reacts pullulan and the silylating agent in one of or a mixture of both of N-methyl-2-pyrrolidone and N-ethyl-2-pyrrolidone described above. No particular limitation is imposed on the order of addition of pullulan and the silylating agent to the solvent. Preferably, however, pullulan is dissolved in the solvent, and the silylating agent is then added dropwise to the solution to conduct the reaction.

The amount of the silylating agent to be used may preferably be from 2- to 4-fold moles per mole of pullulan. Use of the silylating agent in an amount smaller than 2-fold moles provides the resulting silylated pullulan with insufficient water resistance. On the other hand, use of the silylating agent in an amount greater than 4-fold moles per mole of pullulan is uneconomical. Reaction conditions may preferably consist of from 50 to 140° C. and from 1 to 15 hours.

In the above-described reaction, one of or both of N-methyl-2-pyrrolidone and N-ethyl-2-pyrrolidone is used as the solvent. The amount of the reaction solvent to be used may be preferably from 3- to 20-fold by weight, notably from 4- to 15-fold by weight based on the raw material pullulan. Use of the reaction solvent in an amount smaller than 3-fold by weight provides the reaction mixture with excessively high viscosity so that the reaction mixture cannot be stirred sufficiently. On the other hand, use of the reaction solvent in an amount greater than 20-fold by weight leads to a reduction in reactivity, and therefore, is inefficient.

If the amount of the solvent is small, a good solvent for silylated pullulan, such as benzene, toluene, xylene or isopropyl alcohol, especially preferably, toluene may be added before or after the reaction or in the course of the reaction for the purpose of lowering the viscosity of the reaction system (promoting the reaction and improving the transport performance of the reaction mixture). The use of toluene or the like is not essential but, when employed, toluene or the like may be used preferably as much as from approx. 5 to 100 parts by weight per 100 parts by weight of the reaction solvent. Use of toluene or the like in an excessive amount leads to an increase in the amount of a precipitation solvent such as methanol to be used after completion of the reaction, and therefore, is uneconomical and is not preferred.

After completion of the reaction, the reaction solvent is eliminated from the resulting reaction mixture to obtain silylated pullulan. When high-purity silylated pullulan is desired, however, it can be obtained by allowing the above-described reaction mixture to cool down and pouring it into a poor solvent for silylated pullulan, for example, into from approx. 1 to 20 volumes of methanol based on the reaction mixture to precipitate the silylated pullulan, collecting the precipitated silylated pullulan by filtration, immersing the resulting filter cake in methanol, collecting the silylated pullulan by filtration, washing the silylated pullulan with methanol, and then fully eliminating the reaction solvent.

When silylated pullulan of still higher purity is required, the silylated pullulan obtained as described above is re-dissolved in a good solvent for silylated pullulan, for example, toluene or isopropyl alcohol, and methanol washing is then conducted in a similar manner as described above to fully eliminate the reaction solvent from the purified silylated pullulan. The thus-obtained silylated pullulan is dried in a conventionally-used fan dryer or vacuum dryer, preferably, in a vacuum dryer to obtain silylated pullulan of the present invention in a dried form. When there is a need to fully eliminate the reaction solvent still further, the reaction solvent still remaining in the silylated pullulan can be fully eliminated by once finely disintegrating the dried silylated pullulan, washing the finely-disintegrated silylated pullulan with methanol in a similar manner as described above, and then drying the washed silylated pullulan in a similar manner as described above. In this manner, the content of the reaction solvent in dried silylated pullulan to be obtained finally can be controlled to 10 ppm, which is a detection limit, or lower. The disintegration of the resulting, purified silylated pullulan can be conducted by a conventionally-employed hammer mill, jet mill, ball mill, vibrating mill or the like.

The content of trimethylsilyl groups in purified silylated pullulan to be obtained as described above can be adjusted depending on the application of the purified silylated pullulan (specifically, whether it is applied to a water-based cosmetic preparation or to an oil-based cosmetic preparation). For oil-based applications, the content of trimethylsilyl groups in silylated pullulan may be preferably 30 wt % or higher, with from 50 to 58 wt % being more preferred. When silylated pullulan is applied to water-based cosmetic preparations, on the other hand, the content of trimethylsilyl groups in silylated pullulan can also be lower than 30 wt %.

By the above-described production process of the present invention, high-purity silylated pullulan can be obtained with a small residual amount of the reaction solvent. This silylated pullulan is useful as a raw material for cosmetic products. Among such cosmetic products, oil-based cosmetic preparations generally have excellent water resistance and adherence, and are widely used. The addition of the silylated pullulan of the present invention to the oil-based cosmetic preparations can provide the oil-based cosmetic preparations with still better water resistance and adherence.

No particular limitation is imposed on the cosmetic preparations to which the silylated pullulan according to the present invention can be added. In general, oily bases composed of a semi-solid oil and/or a liquid oil and/or a solid oil, and oily bases obtained by further adding an oily gelling agent can be used. Cosmetic preparations can also be produced by mixing and dispersing commonly-employed cosmetic additives in such oil bases.

The molecular weight of silylated pullulan according to the present invention, which is to be added to an oil-based cosmetic preparation, may be adjusted depending on the amount of each oily base to be mixed and properties such as a viscosity to be needed, and if necessary, also depending on the molecular weight of the raw material pullulan, and may be added preferably in amounts of from 0.005 wt % to 30 wt % to oil-based cosmetic preparations.

No particular limitation is imposed on the liquid oil or semi-solid oil ingredient in each oil-based cosmetic preparation to which silylated pullulan according to the present invention is to be added, insofar as it is employed in general cosmetic preparations. Those having melting points of 25° C. or lower or so are preferred. Examples include animal or vegetable oils, aliphatic hydrocarbons, higher fatty acids, ester oils, higher alcohols, silicones, and the like.

More specific examples include animal or vegetable oils such as avocado oil, almond oil, olive oil, sunflower oil, turtle oil, castor oil, jojoba oil and mink oil; liquid paraffins such as hydrogenated polyisobutene and polybutene, and aliphatic hydrocarbons such as volatile isoparaffins and squalane; higher fatty acids such as oleic acid and isostearic acid; and ester oils such as isopropyl myristate, isopropyl palmitate, isostearyl malate, trimethyl citrate, cetyl isooctanate, octyldodecyl myristate and isocetyl stearate.

Also included are glycerides such as glyceryl trioctanoate and glyceryl triisostearate; higher alcohols such as oleyl alcohol and isostearyl alcohol; silicones such as dimethylpolysiloxane and methylphenylpolysiloxane; glycerin fatty acid esters such as lanolin, petrolatum, octyldocecyl myristate, cetyl 2-ethylhexanoate, and triglyceryl 2-ethylhexanoate; and propylene glycol fatty acid esters such as propylene glycol dicaprylate. At least one of these liquid or semi-solid oils can be used.

No particular limitation is imposed on the solid oil insofar as it is usable in general cosmetics. One having a melting point of 40° C. or higher or so is preferred. Usable examples include waxes such as ethylene-propylene copolymer, carnauba wax, candelilla wax, silicone wax, paraffin wax, polyethylene wax, ceresin wax, microcrystalline wax, bees wax, Japan wax, hydrogenated castor oil, pentaerythritol rosinate, stearic acid, lauric acid, myristic acid, behenic acid, stearyl alcohol, lauryl alcohol, and the like. At least one of these solid oils can be used.

No particular limitation is imposed on the oily gelling agent insofar as it gels the oily base, performs an adjustment in accordance with the application and is commonly usable in general cosmetic preparations. Examples include 12-hydroxystearic acid having a hydroxyl group, clay minerals such as organically-modified montmorillonite clay, dextrin palmitates such as dextrin fatty acid esters, lipophilic sucrose fatty acid esters, fructooligosaccharide fatty acid esters, silicic acid anhydride, metallic soaps such as calcium stearate and calcium palmitate, and the like. At least one of these oily gelling agents can be used.

Concerning the oily gelling agent, the term "silicic acid anhydride" means silicic acid anhydride useful as a raw material for general cosmetic preparations, and can be nonporous, porous, spherical, fumed or so. It is also preferred to use, for example, hydrophobized, fumed silicic acid anhydride. As the metallic soaps, aluminum 12-hydroxystearate, aluminum isostearate, calcium stearate and the like can be used. Concerning the organically-modified clay mineral, it is also a preferred mode to add one obtained by treating a waterswellable clay mineral with a quaternary ammonium salt.

The above-described solid oils and/or oily gelling agents can each be used singly, or at least one of them can be used. More preferably, an oily base can be prepared by mixing an oil base composed of the above-described semi-solid oil and/or liquid oil with another oil base composed of the solid oil and/or oily gelling agent. No particular limitation is imposed on the mixing amount of the solid oil and/or oily gelling agent, and the solid oil and/or oily gelling agent may be added preferably in an amount of from 0.1 to 30 wt %, more preferably in an amount of from 0.5 to 15 wt % based on the oily base.

To the oil-base cosmetic preparation with silylated pullulan of the present invention mixed therein, ingredients other than the above-described respective oily ingredients can also be added as needed. It is also a preferred embodiment to add, for example, one or more of pigments, surfactants, antioxidants, ultraviolet absorbers, film-forming agents, humectants, preservatives, anti-algae agents, glitters, fragrances, beauty ingredients, colorants and the like.

The oil-based cosmetic with the silylated pullulan of the present invention mixed therein can be formulated into various product forms depending on the purposes. The oil-base cosmetic can be formulated, for example, into forms such as solid, paste and liquid forms. Described specifically, the silylated pullulan of the present invention can be used in lipsticks, lip creams, lip glosses, foundations, rouges, eye colors, eyeliners, mascaras, oil cleansings, nail treatments, hair cosmetics such as hair dressings, sunscreen lotions, and the like. It is to be noted that the above-described oil-based cosmetic preparations can be produced by general formulation methods for cosmetic preparations and no particular limitation is imposed on their formulation methods.

EXAMPLES

The present invention will next be described more specifically based on examples.

Example 1

After pullulan ("PI-10", trade name; product of Hayashibara Shoji, Inc.) (12 g) was dispersed in NMP (product of Mitsubishi Chemical Corporation) (100 g), stirring was conducted under heat at 100° C. for 1 hour or longer to dissolve the pullulan. Subsequent to the dissolution of the pullulan, N,O-bistrimethylsilylacetamide ("DYNASYLAN BSA", product of Degussa AG) (45 g) was added dropwise over approx. 1 hour while maintaining the temperature at from 100 to 110° C. After completion of the dropwise addition, stirring was continued further for 4 hours at temperatures of from 100 to 110° C. to conduct a silylation reaction. A gel-like precipitate was observed during the reaction, although no problem was posed for the stirring.

The reaction mixture, which had been allowed to cool down to room temperature after completion of the reaction, was poured into methanol (200 g) to completely precipitate silylated pullulan. The precipitated silylated pullulan was collected by filtration and then subjected to methanol immersion and washing treatment, and the silylated pullulan was again collected by filtration. The silylated pullulan was next re-dissolved in isopropyl alcohol (60 g), and the resulting solution was poured into methanol to cause re-precipitation. After the operation consisting of the collection by filtration, the methanol immersion and washing treatment and the collection by filtration was repeated twice, drying was conducted at 80° C. for 10 hours in a vacuum dryer to obtain trimethylsilyl pullulan (27.1 g). The content of silicon (Si) as determined by decomposition with sulfuric acid and ignition ashing was 22.1 wt % (58 wt % in terms of trimethylsilyl groups in the silylated pullulan).

Example 2

After pullulan ("PI-10", trade name; product of Hayashibara Shoji, Inc.) (12 g) was dispersed in NEP (product of BASF AG) (100 g), stirring was conducted under heat at 100° C. for 1 hour or longer to dissolve the pullulan. Subsequent to the dissolution of the pullulan, N,O-bistrimethylsilylacetamide ("DYNASYLAN BSA", product of Degussa AG) (45 g) was added dropwise over approx. 1 hour while maintaining the temperature at from 100 to 110° C. After completion of the dropwise addition, stirring was continued further for 4 hours at temperatures of from 100 to 110° C. to conduct a silylation reaction. A gel-like precipitate was observed during the reaction, although no problem was posed for the stirring.

The reaction mixture, which had been allowed to cool down to room temperature after completion of the reaction, was poured into methanol (200 g) to completely precipitate silylated pullulan. The precipitated silylated pullulan was collected by filtration and then subjected to methanol immersion and washing treatment, and the silylated pullulan was again collected by filtration. The silylated pullulan was next re-dissolved in isopropyl alcohol (60 g), and the resulting solution was poured into methanol to cause re-precipitation. After the operation consisting of the collection by filtration, the methanol immersion and washing treatment and the collection by filtration was repeated twice, drying was conducted at 80° C. for 10 hours in a vacuum dryer to obtain trimethylsilyl pullulan (23.2 g). The content of silicon (Si) as determined by decomposition with sulfuric acid and ignition ashing was 21.1 wt % (55 wt % in terms of trimethylsilyl groups in the silylated pullulan).

Example 3

After pullulan ("PI-20", trade name; product of Hayashibara Shoji, Inc.) (12 g) was dispersed in a mixed solvent of NMP (50 g) and NEP (50 g), stirring was conducted under heat at 100° C. for 1 hour or longer to dissolve the pullulan.

Subsequent to the dissolution of the pullulan, N,O-bistrimethylsilylacetamide ("DYNASYLAN BSA", product of Degussa AG) (45 g) was added dropwise over approx. 1 hour while maintaining the temperature at from 100 to 110° C., followed by dropwise addition of toluene (50 g) over approx. 1 hour. After completion of the dropwise addition, stirring was continued further for 3 hours at temperatures of from 100 to 110° C. to conduct a silylation reaction. No gel-like precipitate was observed during the reaction.

The reaction mixture, which had been allowed to cool down to room temperature after completion of the reaction, was poured into methanol (300 g) to precipitate silylated pullulan. The precipitated silylated pullulan was collected by filtration and then subjected to methanol immersion and washing treatment, and the silylated pullulan was again collected by filtration. The silylated pullulan was next re-dissolved in toluene (60 g), and the resulting solution was poured into methanol to cause re-precipitation. After the operation consisting of the collection by filtration, the methanol immersion and washing treatment and the collection by filtration was repeated twice, drying was conducted at 80° C. for 10 hours in a vacuum dryer to obtain trimethylsilyl pullulan (26.6 g). The content of silicon (Si) as determined by decomposition with sulfuric acid and ignition ashing was 21.8 wt % (57 wt % in terms of trimethylsilyl groups in the silylated pullulan).

Example 4

After pullulan ("PI-20", trade name; product of Hayashibara Shoji, Inc.) (12 g) was dispersed in NMP (100 g), stirring was conducted under heat at 100° C. for 1 hour or longer to dissolve the pullulan. Subsequent to the dissolution of the pullulan, N,O-bistrimethylsilylacetamide ("DYNASYLAN BSA", product of Degussa AG) (45 g) was added dropwise over approx. 1 hour while maintaining the temperature at from 100 to 110° C., followed by dropwise addition of toluene (50 g) over approx. 1 hour. After completion of the dropwise addition, stirring was continued further for 3 hours at temperatures of from 100 to 110° C. to conduct a silylation reaction. No gel-like precipitate was observed during the reaction.

The reaction mixture, which had been allowed to cool down to room temperature after completion of the reaction, was poured into methanol (300 g) to precipitate silylated pullulan. The precipitated silylated pullulan was collected by filtration and then subjected to methanol immersion and washing treatment, and the silylated pullulan was again collected by filtration. The silylated pullulan was next re-dissolved in toluene (60 g), and the resulting solution was poured into methanol to cause re-precipitation. After the operation consisting of the collection by filtration, the methanol immersion and washing treatment and the collection by filtration was repeated thrice, drying was conducted at 90° C. for 12 hours in a vacuum dryer to obtain trimethylsilyl pullulan (26.7 g). The content of silicon (Si) as determined by decomposition with sulfuric acid and ignition ashing was 21.8 wt % (57 wt % in terms of trimethylsilyl groups in the silylated pullulan).

[Quantitative Analysis of Residual Solvent]

The silylated pullulans obtained above in Examples 1 to 4 were quantitatively analyzed for residual solvents by gas chromatograph/mass spectroscope (GC/MS).

(Measurement Conditions)
Column: DB-1 (0.25 mm in diameter×30 m, film thickness: 0.25 μm)
Carrier: He 36 cm/sec, 7.1 psi, 1 mL/min
Oven: 40 to 200° C. (20° C./min)
Injection: Split (5:1)
Detector: MSD

TABLE 1

Measurement Results

| | Example 1 | Example 2 | Example 3 | Example 4 |
|---|---|---|---|---|
| NMP | Not detected[3] | — | Not detected | Not detected |
| NEP | —[4] | Not detected | Not detected | — |
| BSA[1] | Not detected | Not detected | Not detected | Not detected |
| Methanol | 10 ppm | 15 ppm | 10 ppm | Not detected |
| IPA[2] | Not detected | Not detected | — | — |
| Toluene | — | — | Not detected | Not detected |

[1]BSA: N,O-Bistrimethylsilylacetamide
[2]IPA: Isopropyl alcohol
[3]Not detected: lower than 10 ppm, 10 ppm: Detection limit by GC/MS
[4]"—" is shown where no solvent was used.

Application Example 1

The silylated pullulans obtained in Examples 1-4 were formulated into mascara samples in accordance with the following mixing proportions and formulation method.
[Formula]
a. Silylated pullulan 5 wt %
b. Light liquid isoparaffins 72 wt %
c. Dextrin palmitate 2 wt %
d. Carnauba wax 3.5 wt %
e. Aluminum 12-hydroxystearate 4.5 wt %
f. Silicic acid anhydride 4 wt %
g. Propyl parahydroxybenzoate 0.05 wt %
h. Black iron oxide 5.95 wt %
i. Titanium oxide 3 wt %
[Formulation Method]

The ingredient c and ingredient d were caused to melt under heat. To the resulting melt, a solution of the ingredient a in the ingredient b was added, and mixing was conducted. The ingredients e, f, g, h and i were then added respectively to the resultant mixture, followed by mixing into a uniform melt. Subsequently, the melt was filled in a container to provide an intended mascara sample.
[Assessment]

In a sensory test of samples obtained as described above, they were assessed for use feel, its retention and uniformity. As a result, all the samples were found to be good in use feel, its retention and uniformity.

Application Example 2

The silylated pullulans obtained in Examples 1-4 were formulated into eyeliner samples in accordance with the following mixing proportions and formulation method.
[Formula]
a. Silylated pullulan 7 wt %
b. Carnauba wax 3 wt %
c. Light liquid isoparaffins 1.5 wt %
d. Silicic acid anhydride 3.5 wt %
e. Propyl parahydroxybenzoate 0.05 wt %
f. Yellow iron oxide 4 wt %
g. Black iron oxide 6.95 wt %
h. Titanium oxide 4 wt %
[Formulation Method]

The ingredient b and a portion of the ingredient c were caused to melt under heat. To the resulting melt, a solution of the ingredient a in the rest of the ingredient c was added, and mixing was conducted. The ingredients d, e, f, g and h were then added respectively to the resultant mixture, followed by mixing into a uniform melt. Subsequently, the melt was filled in a container to provide an intended eyeliner sample.

[Assessment]

In a sensory test of samples obtained as described above, they were assessed for use feel, its retention and uniformity. As a result, all the samples were found to be good in use feel, its retention and uniformity.

INDUSTRIAL APPLICABILITY

According to the present invention, it is possible to provide a simpler, easier and more efficient process for the production of high-purity silylated pullulan than the conventional process. In particular, the present invention does not use any offensively odorous solvent such as pyridine unlike the conventional technology, is free of concern about such an offensively odorous ingredient, and does not require any substantial labor or cost for the elimination of such an offensively odorous ingredient.

The invention claimed is:

1. A process for producing silylated pullulan, comprising:
   (i) dissolving pullulan in only one of N-methyl-2-pyrrolidone, N-ethyl-2-pyrrolidone or a mixture thereof to form a solution;
   (ii) adding dropwise N,O-bis(trimethylsilyl)acetamide to the solution of (i) to react with the pullulan to obtain a solution of silylated pullulan;
   (iii) combining the solution of (ii) with isopropyl alcohol;
   (iv) pouring the resulting solution of (iii) into methanol to precipitate the silylated pullulan; and
   (v) desolvating the precipitated silylated pullulan.

2. The process according to claim 1 further comprising: drying silylated pullulan by a method comprising repeating once or more an operation that dries, disintegrates and re-dries the silylated pullulan of claim 1.

3. The process according to claim 1, further comprising a further purifying process following (v), the further purifying process comprising:
   (vi) re-dissolving the silylated pullulan in isopropyl alcohol followed by methanol washing to precipitate the silylated pullulan,
   (vii) isolating and drying the silylated pullulan of (vi) in a fan dryer or vacuum dryer to obtain dried silylated pullulan,
   (viii) finely disintegrating the dried silylated pullulan of (vii),
   (ix) washing the finely-disintegrated silylated pullulan of (viii) with methanol, and
   (x) isolating and drying the washed silylated pullulan of (ix),
   wherein the content of N-methyl-2-pyrrolidone and/or N-ethyl-2-pyrrolidone in the silylated pullulan of (x) is 10 ppm or lower.

* * * * *